United States Patent [19]
Nakahama et al.

[11] Patent Number: 5,854,279
[45] Date of Patent: Dec. 29, 1998

[54] THERAPEUTIC AGENT FOR DERMATOSIS

[75] Inventors: Akiko Nakahama, Tokyo; Koukichi Harada, Ibaraki; Toshihiko Yamauchi, Ibaraki; Takashi Yamanaka, Ibaraki; Isao Yamatsu, Ibaraki, all of Japan

[73] Assignee: Eisai Co., Ltd, Tokyo, Japan

[21] Appl. No.: 846,478

[22] Filed: May 1, 1997

[30]  Foreign Application Priority Data

Jun. 4, 1996  [JP]  Japan .................................. 8-141445

[51] Int. Cl.$^6$ .................................................. A01N 43/16
[52] U.S. Cl. ........................... 514/453; 514/844; 514/846
[58] Field of Search ..................................... 514/453, 844, 514/846

[56]  References Cited

U.S. PATENT DOCUMENTS

| | | | |
|---|---|---|---|
| 4,737,518 | 4/1988 | Nomura et al. ........................... | 514/476 |
| 5,605,927 | 2/1997 | Korth ...................................... | 514/453 |

FOREIGN PATENT DOCUMENTS

| | | |
|---|---|---|
| 0353474A3 | 2/1990 | European Pat. Off. . |
| 91 18608 | 12/1991 | WIPO . |

OTHER PUBLICATIONS

Merlos et al., Br. J. Pharmacol., 104, 990–994 (1991).
Inagaki et al., J. Pharmacobio–Dyn., 13, 272–277 (1990).
Hayashi et al., Japan. J. Pharmacol., 44, 127–134 (1987).
Woodward et al., J. Pharmacology and Experimental Therapeutics, 272 (2) 758–765 (Feb. 1995).
Tsushima, et al; "Chem. Pharm. Bull." 32 (7), 2700–2713 (1984) ; Synthesis and Biological Activities of N–Alkyl– and N–Alkenylcarbamoyl Phospholipids.

*Primary Examiner*—Terressa Mosley
*Attorney, Agent, or Firm*—Birch, Stewart, Kolasch and Birch, LLP

[57]  ABSTRACT

The present invention provides a therapeutic agent for fundamentally preventing, treating or ameliorating dermatosis, such as, non-infectious dermatosis, which include psoriasis and atopic dermatitis. The therapeutic agent comprises a glycerol derivative represented by the formula (I):

$$R^1 \smile \underset{OCH_3}{\overset{}{\diagup}} \smile O \smile A \smile \underset{O}{\overset{}{\diagup}} NHC_{18}H_{37} \qquad (I)$$

wherein A is a group represented by the formula:

(piperidine-containing group)

or single bond;
$R^1$ is a group represented by the formula:

(pyridinium-containing group with $R^2$, CO, N, O, $X^-$, $C_2H_5$)

wherein $R^2$ is a methoxyphenyl group or methyl group, X is an atom or atomic group which may become an anion or a group represented by the formula:

(thiazolium-containing phosphate group)

or a pharmacologically acceptable salt thereof as an active ingredient.

5 Claims, 2 Drawing Sheets

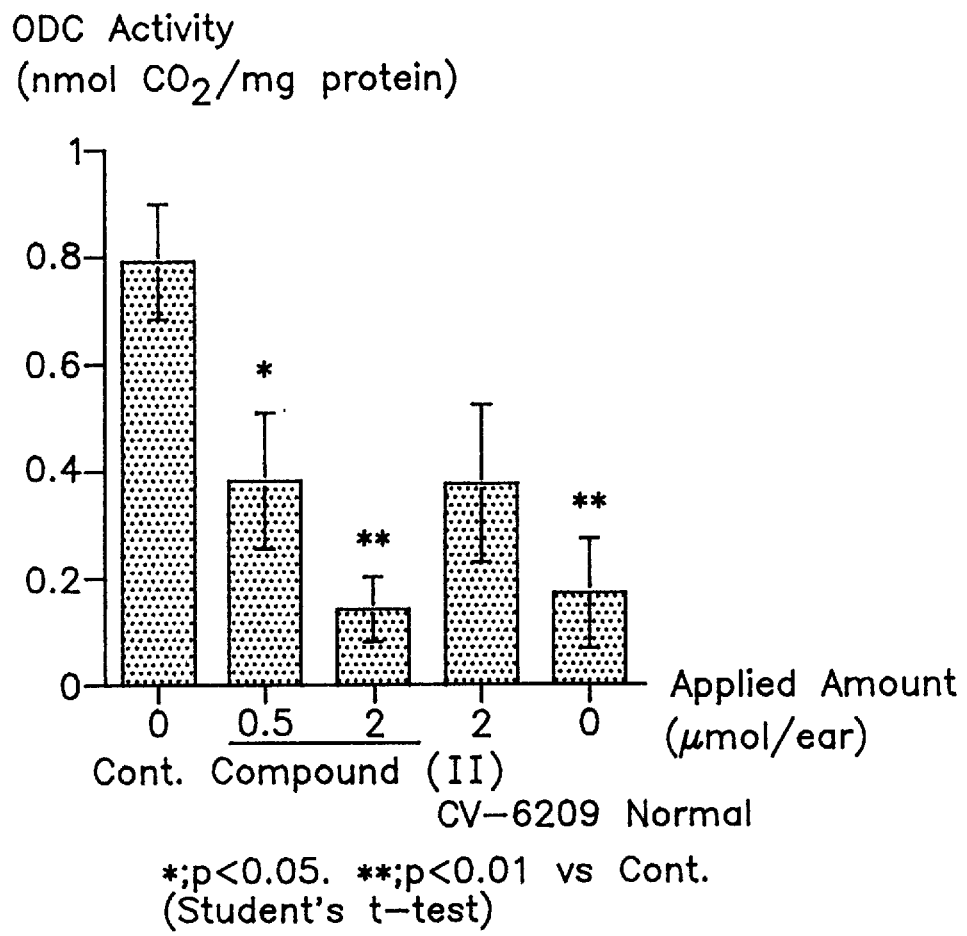

THERAPEUTIC AGENT FOR DERMATOSIS

BACKGROUND OF THE INVENTION

1. Field of the Invention

The present invention relates to a therapeutic agent for prevention, treatment or amelioration of dermatosis excluding itching, more preferably, non-infectious dermatosis, still more preferably, psoriasis or atopic dermatitis.

Recently, with environmental pollution or the change of life-style, eating habits, or the like, morbidity of dermatosis has been increasing. Particularly, non-infectious dermatosis has been significantly increasing. In such dermatosis, patients suffering from psoriasis or atopic dermatitis are rapidly increasing in number. Both diseases are characteristically inveterate and highly recurrent even after once cured.

The mechanism of crisis of non-infectious dermatosis is mostly unknown, and there are no fundamental treatment. Accordingly, these diseases are treated by symptomatic therapy based on improvement of environment, dietetic therapy, guidance of life-style under the present conditions. Therefore, there has been strongly required highly safe remedies for prevention, treatment or amelioration, which may provide a fundamental therapy.

Itching partly exhibits clinical conditions resembling to those of atopic dermatitis, but both diseases are completely different, and readily diagnosed and distinguishable. The treatment methods thereof are also different. Accordingly, the present invention is absolutely different from the invention relating to itching disclosed in WO91/18608.

2. Prior Art

For example, psoriasis is treated basically with insolation and dietetic therapy, and internal preparations such as methotrexate, retinoid, cyclosporin, active vitamin $D_3$, adrenocortical hormone and external preparations such as adrenocortical hormone, active vitamin $D_3$ are also used for the treatment.

Furthermore, atopic dermatitis is treated basically with countermeasure of allergen, skin care and guidance of life style, and external preparation of adrenocortical hormone are mainly used for symptomatic therapy.

However, methotrexate, which is used for psoriasis, is originally an anticancer agent, and may induce severe side effects such as inhibition of bone marrow function, hepatic or renal dysfunction. Accordingly, this therapy is used only when the well-experienced physicians estimate it to be proper.

Since retinoid (etretinate) has such problems that teratogenicity, it can not be applied to women who are or may be pregnant. In addition, since it is known to have tendency to induce hepatopathy, it is limited to use only when there is no effective treatment and the patients are seriously ill. Actually, it is difficult to use this therapeutic agent.

Cyclosporin is originally an inhibitor of immune reaction (rejection) accompanied with graft transplantation, etc., and the level of absorption upon oral administration varies depending on individuals, therefore the concentration of the drug in blood may be increased, causing side effect such as shock, etc. Therefore, it should be carefully administered. In addition, it has problems of causing side effect such as renal hypofunction and hypertension.

Since active vitamin $D_3$ has problems of high frequency of causing hypercalcemia as a side effect, it should be administered while concentration of calcium in blood is periodically checked.

Adrenocortical hormone (betamethasone, prednisolone, dexamethasone, etc.) are adrenocortical hormones, and have problems to cause various side effects such as induction of infection due to decrease of immunity, cryptorrhea, chromatosis upon application for a long period of time.

As mentioned above, since there is no fundamental therapeutic agent for psoriasis under the present conditions, and symptomatic therapy has various problems on safety, thus, novel remedies for prevention, treatment or amelioration of the disease has been desired.

In addition, adrenocortical hormone used for treatment of atopic dermatitis has numerous side effect as mentioned above, and is not suitable for application for a long period of time.

In addition, zinc ointment, urea ointment, non-steroidal external preparation, etc. have been used, but none of them are expected to have sufficient therapeutic effect for severe dermatitis because they have less anti-inflammation effect compared with that of adrenocortical hormone.

Since there is no fundamental therapeutic agent for atopic dermatitis under the present conditions, and symptomatic therapy has various problems on safety or therapeutic effect, thus, novel remedies for prevention, treatment or amelioration of the disease has been required.

Therefore, the present inventors have studied intensively on compounds satisfying the above demands. As the results, they have found that the above glycerol derivative (I) can thoroughly prevent, treat and ameliorate dermatosis, more preferably, non-infectious dermatosis, still more preferably, psoriasis or atopic dermatitis, and further they are highly safe and can attain the desired object as clinically effective therapeutic agent for prevention, treatment or amelioration of dermatosis. Thus, the present invention has accomplished. Accordingly, an object of the present invention is to provide a therapeutic agent for fundamental prevention, treatment or amelioration of dermatosis, more preferably, non-infectious dermatosis, still more preferably, psoriasis or atopic dermatitis.

SUMMARY OF THE INVENTION

The glycerol derivative (I) according to the present invention is a compound described in EP-0353474 A1, Chem. Pharm. Bull., 32(7), 2700–13(1984) and U.S. Pat. No. 4,737,518. They discloses a therapeutic agent having anti-platelet activating factor (PAF) effect for prevention or amelioration of DIC, shock, etc. After further study, the present inventors have unexpectedly found that it also has effect for prevention, treatment or amelioration of dermatosis, and have attain the present invention.

The glycerol derivative (I) according to the present invention is represented by the following formula:

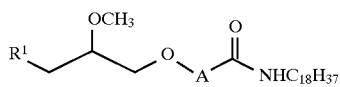

In the formula, A is a group represented by the formula:

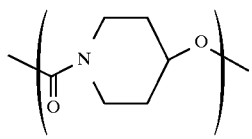

or single bond, $R^1$ is a group represented by the following formula:

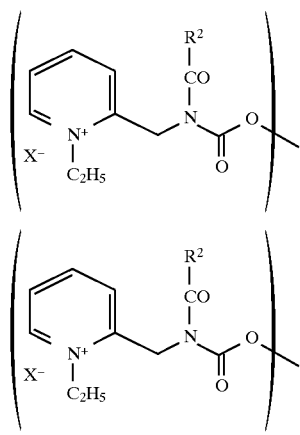

wherein $R^2$ represents a methoxyphenyl or methyl group, X is an atom or atomic group which may become an anion, or group represented by the following formula:

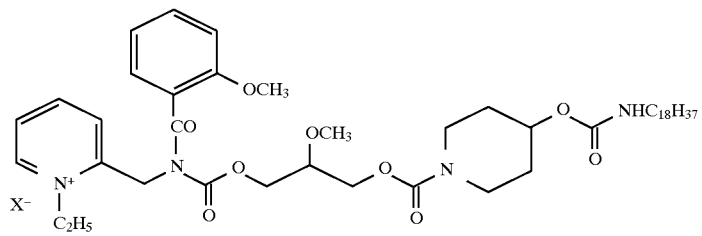

More particularly, the glycerol derivative (I) according to the present invention includes the following compounds but are not intended to be limited to them.

(1) 1-ethyl-2-[N-(2-methoxy)benzoyl-N-{2-methoxy-3-(4-octadecylcarbamoyloxy) piperidinocarbonyloxypropoxy} carbonyl]aminomethyl pyridinium salt;

(2) 2-(2-acetyl-6-methoxy-3,9-dioxo-4,8-dioxa-2,10-diazaoctacosa-1-yl)-1-ethyl pyridinium salt;

(3) 3-(4-hydroxy-7-methoxy-10-oxo-3,5,9-trioxa-11-aza-4-phosphanonacosa-1-yl)thiazolium.

Among these compounds, more preferred compound is 1-ethyl-2-[N-(2-methoxy)benzoyl-N-{2-methoxy-3-(4-octadecylcarbamoyloxy) piperidinocarbonyloxypropoxy} carbonyl]aminomethylpyridinium salt represented by the following formula:

wherein X is as defined above.

Particularly preferably, glycerol derivative (I) is 1-ethyl-2-[N-(2-methoxy)benzoyl-N-{(2R)-2-methoxy-3-(4-octadecylcarbamoyloxy)piperidinocarbonyloxypropoxy}carbonyl]aminomethyl pyridinium chloride (II) of the following formula:

DETAILED DESCRIPTION OF THE INVENTION

The present invention is a therapeutic agent for prevention, treatment or amelioration of dermatosis which comprises the above compound or a pharmacologically acceptable salt thereof as an active ingredient. A pharmacologically acceptable salt used herein depends on X in the formula of the above glycerol derivative (I). X means an atom or atomic group which may become an anion. Example of X- includes counter ion in quaternary ammonium salt. Such counter ion includes, more concretely, chlorine ion, bromine ion, iodine ion, sulfate ion, nitrate ion, phosphate ion, perchlolate ion, methanesulfonate ion, ethanesulfonate ion, benzenesulfonate ion, p-toluenesulfonate ion, camphorsulfonate ion, hydroxide ion. Among them, chlorine ion is more preferred, but not to be limited to it.

The present invention relates to a method for preventing, treating and ameliorating dermatosis except for itching comprising administering a pharmacologically effective amount of a glycerol derivative represented by the formula (I) or a pharmacologically acceptable salt thereof to a person suffering from the dermatosis except for itching.

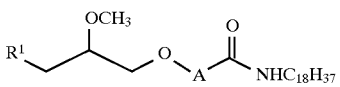

wherein A is a group represented by the formula:

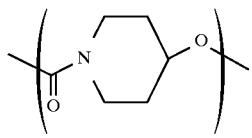

or single bond;

$R^1$ is a group represented by the formula:

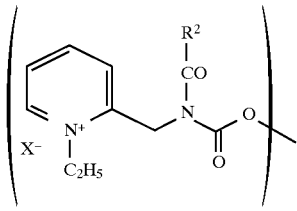

wherein $R^2$ is a methoxyphenyl group or methyl group, X is an atom or atomic group which may become an anion or group represented by the formula:

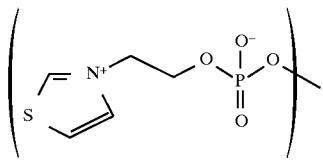

The present invention relates to a use of a glycerol derivative represented by the formula (I) or a pharmacologically acceptable salt thereof for manufacturing a preventing, treating and ameliorating medicament for dermatosis except for itching.

The glycerol derivative (I) according to the present invention may be produced according to the method described in the above reference (EP-0353474 A1), Chem. Pharm. Bull., 32(7), 2700–13(1984), JP-A-2-277505).

The dosage form of the compound of the present invention includes, for example, external preparation such as ointment, cream, lotion, patch; oral preparation such as powders, subtilized granules, granules, tablets, coated tablets, capsules; suppository and preparations for injection. Application route of the present invention is not limited, but the external preparation is more preferred. In preparation of any forms, they can be produced by using conventional carrier according to the conventional method.

That is, when the external preparation is produced, the processes are not particularly limited, and it may be produced according to the conventional method. For the preparation, materials for base used may be those conventionally used for drugs, quasi-drugs, cosmetics, etc.

The materials used for base include, for example, animal and vegetable oil, mineral oil, ester oil, wax, higher alcohols, fatty acids, silicone oil, surfactants, phospholipids, alcohols, polyhydric alcohols, water-soluble polymers, clay minerals, purified water. As needed, pH controller, antioxidant, chelating agents, antiseptic and antifungal agents, colorant, perfume and the like may be further added. However, the materials for base of the external preparation of the present invention are not limited to them. Moreover, blood flow promoter, antibiotics, aseptic, antiphlogistic agent, cell activator, vitamins, amino acids, humectants, keratolytic, buffering agents may be compounded if needed. The amount of the base material to be added so as to attain the concentration conventionally set for ordinary external preparations.

Examples of the process for producing the external preparation, concretely, the compound of the present invention, oil phase mixture such as oil and fats and various kinds of water-soluble materials dissolved in purified water are prepared, which are sufficiently mixed by using a high-speed emulsifier as needed. However, it is not to be limited to the above process.

To produce oral preparation, the compound of the present invention is admixed with an excipient, as well as an antioxidant, a binder, a disintegrant, a lubricant, a colorant, a corrigent added as needed, then formed into powders, subtilized granules, granules, tablets, coated-tablets, capsules or the like by the conventional method.

Examples of the excipient include lactose, corn starch, sucrose, glucose, mannitol, sorbitol, crystalline cellulose, silicon dioxide. Examples of the binder include polyvinyl alcohol, polyvinyl ether, methyl cellulose, ethyl cellulose, gum Arabic, tragacanth, gelatin, shellac, hydroxypropylmethyl cellulose, hydroxypropyl cellulose, polyvinylpyrolidone, polypropylene glycol-polyoxyethylene block polymer, meglumine. Examples of the disintegrant include starch, agar, gelatin powder, crystalline cellulose, calcium carbonate, sodium bicarbonate, calcium citrate, dextrin, pectin, carboxymethyl cellulose, calcium. Examples of the lubricant include magnesium stearate, talc, polyethylene glycol, silica, hydrogenated vegetable oil. Examples of the colorant include those accepted to be added to drugs. Examples of corrigent include cocoa powder, l-menthol, aromatic powder, mentha oil, Borneo camphor, powdered cinnamon. These tablets and granules may be coated with sugar coating and optionally with another coating.

In the process for producing the preparation for injection, the compound of the present invention is admixed with, for example, pH controller, solubilizer, isotonic agent, and solubilizing ajuvant, stabilizer, antioxidant, buffering agent as needed, and prepared according to the conventional method.

The clinical dosage of a glycerol derivative (I) of the present invention or a pharmacologically acceptable salt thereof is not limited but varies depending on the conditions, severity, age, complication, area of the diseased part and the like. And generally 0.1 mg to 5,000 mg, preferably 1 mg to 3,000 mg, more preferably, 10 mg to 1,000 mg per day for an adult. Such dosage is transdermally, orally, intravenously, intramuscularly or rectally administered.

As specific examples of the compound of the present invention, the results of acute toxicity test of 1-ethyl-2-[N-(2-methoxy)benzoyl-N-{(2R)-2-methoxy-3-(4-octadecylcarbamoyloxy) piperidinocarbonyloxypropoxy} carbonyl]aminomethyl pyridinium chloride [hereinafter referred to as Compound (II)] will be shown below.

BRIEF DESCRIPTION OF DRAWINGS

FIG. 3 shows the effect on the increase of epidermal TPA-induced ODC activity in the groups treated with Compound (II) and CV-6209. (expressed as mean±standard error)

EXAMPLE

Acute Toxicity Test

Slc:SD rat and Slc:ICR mice (age in week of 6 to 8), each group has 5 male and 5 female, were applied to a toxicity test upon single dosage carried out by intravenous administration. (Medium: physiological saline) The $LD_{50}$ values are summarized in the following table:

TABLE 1

Acute toxicity of 1-ethyl-2-[N-(2-methoxy)benzoyl-N-{(2R)-2-methoxy-3-(4-octadecylcarbamoyloxy) piperidinocarbonyloxypropoxy} carbonyl] aminomethyl pyridinium chloride [Compound (II)] ($LD_{50}$:mg/kg)

| Administration route | Mouse | | Rat | |
|---|---|---|---|---|
| | Male | Female | Male | Female |
| Intravenous Administration | 46.8 mg/kg | 50.0 mg/kg | 18.2 kg/mg | 22.9 mg/kg |

These $LD_{50}$ values are about not less than 50 times as much as the clinical dosage upon intravenous administration. Therefore, the compound of the present invention is extremely safe upon any administration route including other routes.

To show the effect of the present invention, the effect of example, Compound (II), on (1) TPA-induced reaction on earlobe and on (2) mouse epidermal ornithine decarboxylase (ODC) activity are described in below.

(1) Effect on TPA-Induced Earlobe Reaction
(Experimental Method)
1) TPA-Induced Ear Edema The test was conducted according to the method by Carlson et al. (Agents and Actions, 1985, 17(2), p 197–204).

That is, 2 mg of TPA (phorbol 12-myristate 13-acetate, manufactured by Sigma Chemical Co.) and 4 to 100 nmol of Compound (II) or 250 nmol of dexamethasone (manufactured by Sigma Chemical Co.) were dissolved in 20 ml of acetone. The mixture was applied to inner surface of the right earlobe of BALB/c mouse (male, age in week of 8), to induce inflammation. Four hours after TPA application, the mouse was killed by dislocation of cervical vertebrae and the thickness of each right and left earlobe was measured by using a Dial Thickness Gauge (manufactured by Peacock Co., G0.01 to 10 mm) and the difference in thickness between right and left earlobe was considered as edema.

2) Measurement of MPO Activity

Figure 1:
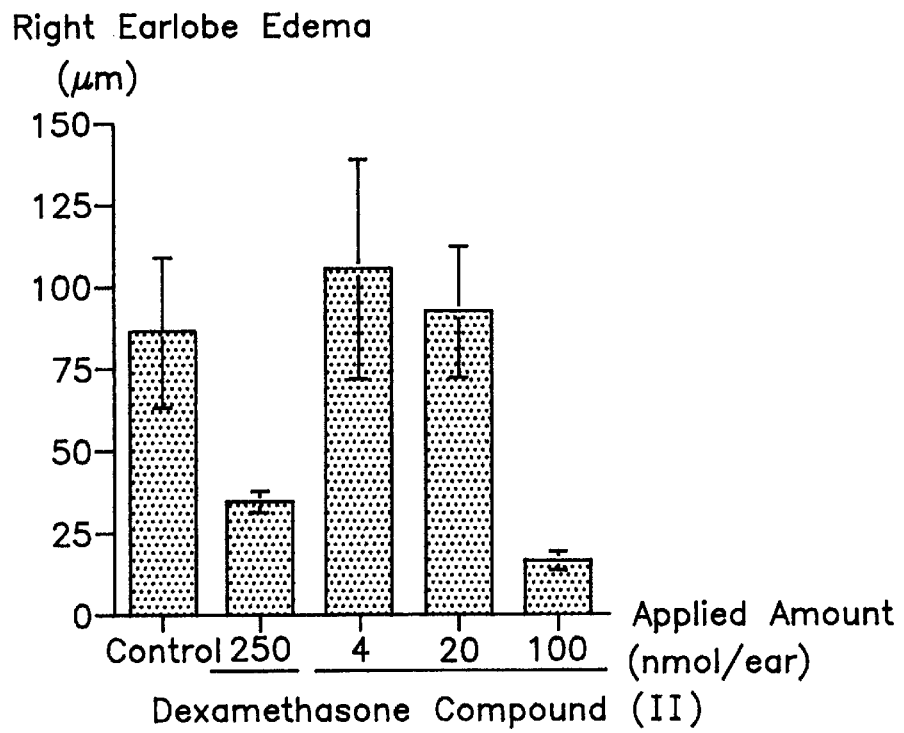
FIG. 1 shows the effect on TPA-induced earlobe edema in the groups treated with Compound (II) and Dexamethasone. (expressed as mean±standard error)

After measurement of edema, MPO (myeloperoxidase) activity of the excised right earlobe was measured by the following method. 1 ml of 0.5% HTAB (hexadecyl trimethylammonium bromide, manufactured by Sigma Chemical Co.)/50 mM potassium phosphate buffer, pH 6.0 was added to the excised right earlobe and homogenized. The supernatant obtained after centrifugation was used as an extract. Measurement of MPO activity in the extract was carried out according to a method using a 96-well plate. That is, reaction was initiated by adding 190 ml of assay buffer (0.167 mg/ml o-dianisidine, manufactured by Sigma Chemical Co.) and 0.0005% $H_2O_2$/50 mM potassium phosphate buffer, pH 6.0) to 10 ml of the extract. Absorbance at 450 nm was measured for 3 minutes at every 10 seconds. The slope of the straight line obtained for 1 minute after 10 seconds from the beginning of the reaction was calculated for every each sample. MPO activity when the slope is 1 is defined as 1 unit (U), and number of unit in the extract was obtained. Further, the amount of protein in the extract was quantified by BIO-RAD PROTEIN ASSAY (manufactured by Bio-Rad Laboratories), and expressed as MPO activity/mg protein.
(Results)
1) Earlobe Edema Dexamethasone (250 nmol/ear) exhibited about 60% significant inhibition for TPA-induced earlobe edema. On the other hand, the compound (II) showed no inhibition at 4, 20 nmol/ear, but about 81% significant inhibition at 100 nmol/ear. (See, Table 2 and FIG. 1.)

TABLE 2

| TPA | Drug | Applied amount/ earlobe | Right earlobe edema ($\mu$m)[a] |
|---|---|---|---|
| 2 $\mu$mol | — | — | 86.3 ± 22.9 |
| 2 $\mu$mol | Dexamethasone | 250 nmol | 34.7 ± 3.3* |
| 2 $\mu$mol | Compound (II) | 4 nmol | 105.9 ± 33.4 |
| 2 $\mu$mol | Compound (II) | 20 nmol | 92.7 ± 19.8 |
| 2 $\mu$mol | Compound (II) | 100 nmol | 16.7 ± 3.0* |

[a]Average of the seven cases ± SEM
*P < 0.05, Student's t-test
2) MPO Activity

Figure 2:
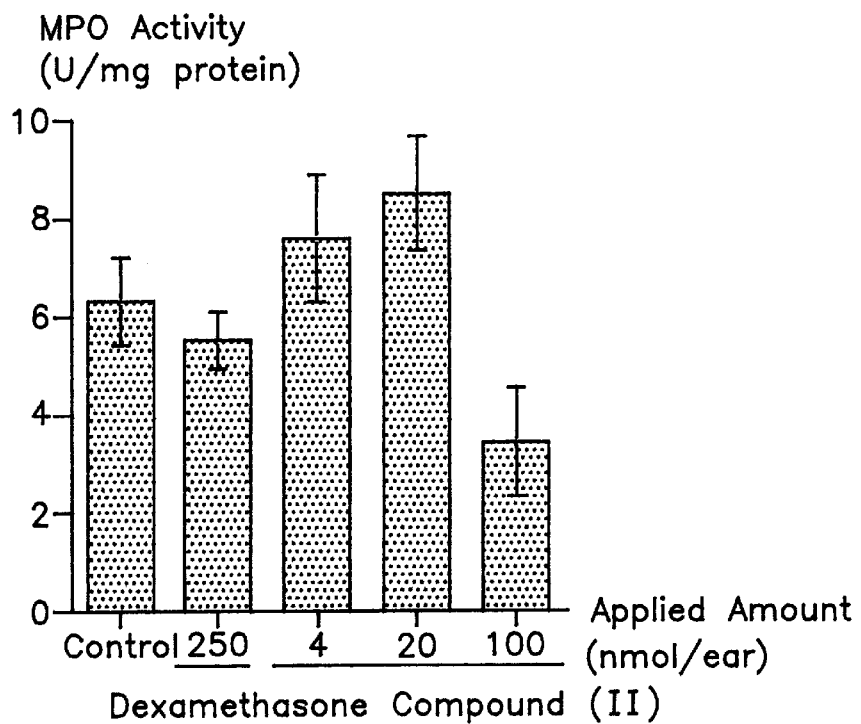
FIG. 2 shows the effect on MPO activity. (expressed as mean±standard error)

Dexamethasone showed about 13% inhibition against MPO activity at 250 nmol/ear. On the other hand, Compound (II) did not show inhibition at 4 or 20 nmol/ear but about 46% inhibition at 100 nmol/ear. (See, Table 3 and FIG. 2.)

TABLE 3

| TPA | Drug | Applied amount/ earlobe | MPO Activity (U/mg, protein)[a] |
|---|---|---|---|
| 2 $\mu$mol | — | — | 6.34 ± 0.90 |
| 2 $\mu$mol | Dexamethasone | 250 nmol | 5.52 ± 0.59 |
| 2 $\mu$mol | Compound (II) | 4 nmol | 7.63 ± 1.30 |
| 2 $\mu$mol | Compound (II) | 20 nmol | 8.51 ± 1.21 |
| 2 $\mu$mol | Compound (II) | 100 nmol | 3.45 ± 1.06 |

[a]Average of the seven cases ± SEM
*P < 0.05, Student's t-test (2) Measurement of Mouse Epidermal Ornithine Decarboxylase (ODC) Activity
(Experimental Method)
1) Induction of ODC Activity The experiment was carried out according to the method by O'Brien et al. (Cancer Research, 1975, 35(2), p 1662–1670).

200 ml of acetone solution containing 17 nmol of TPA (phorbol 12-myristate 13-acetate, manufactured by Sigma) and 0.5 to 2 μmol of Compound (II) or 2-(2-acetyl-6-methoxy-3,9-dioxo-4,8-dioxa-2,10-diazaoctacosa-1-yl)-1-ethylpyridinium salt (customary name; CV-6209, manufactured by Wako Junyaku) was homogeneously applied on the skin of the back (about 8 cm$^2$) of the hairless mouse (strain: SKH/hr-1, female, age in week of 9). After 4.5 hours, mouse was killed by anesthetizing with ether, and skin tissue was excised. The skin tissue was treated at 55° C. for 30 seconds, then ice-cooled and the epidermis was peeled off. To this epidermis, 1 ml of 50 mM sodium phosphate buffer [pH 7.2, 0.4 mM pyridoxal 5-phosphate (manufactured by Sigma), 5 mM dithiothreitol (manufactured by Sigma)] were added, homogenized and then centrifuged at 4° C. and 30,000 g for 30 minutes to obtain a supernatant.

2) Measurement of ODC Activity

ODC activity in the supernatant was measured by $^{14}CO_2$ release from L-[1-$^{14}$C]ornithine (manufactured by Sigma) as an index. A tube containing 50 μl of the above buffer comprising 1 mM L-ornithine and 0.5 mCi L-[1-$^{14}$C] ornithine (manufactured by Amersham) as well as 100 μl of homogenate sample added thereto was rapidly placed into a vial, and sealed. This vial was incubated at 37° C. for one hour, to which was added 0.3 ml of 2M citric acid solution and further incubated for one hour. $^{14}CO_2$ released during this period was trapped by using a filter containing 0.15 ml of NCS solubilizer set in the reaction vial. After removing out the tube, 15 ml of liquid scintillator (ACSII) was added and radioactivity in the vial was measured by using a liquid scintillation counter.

Further, the concentration of protein in the homogenate sample was quantified by using the above BIO-RAD PROTEIN ASSAY, and the amount of the released $^{14}CO_2$/mg protein was calculated and used as an index of ODC activity.
(Results)

As compared with the normal group, the TPA-applied group showed significant increase in the epidermal ODC activity. Compound (II) showed about 52 and 83% significant inhibition to such increase at 0.5 and 2 μmol, respectively. On the other hand, CV-6209 also showed about 53% inhibition at 2 μmol. (See, Table 4 and FIG. 3.)

TABLE 4

| TPA | Drug | Applied amount/ear | Epidermal ODC Activity (nmol CO$_2$/mg protein)[a] |
|---|---|---|---|
| — | — | — | 0.168 ± 0.103** |
| 17 nmol | — | — | 0.793 ± 0.109 |
| 17 nmol | Compound (II) | 0.5 μmol | 0.379 ± 0.130* |
| 17 nmol | Compound (II) | 2 μmol | 0.136 ± 0.066** |
| 17 nmol | CV-6209 | 2 μmol | 0.374 ± 0.147 |

[a] Average of the five cases ± Standard error
*; P < 0.05, **; p < 0.01 vs. TPA control (Student's t-test)

According to the above pharmacological test, it is obvious that the compound of the present invention exhibits excellent prevention, treatment or amelioration effect on dermatosis, preferably prevention, treatment or amelioration effect on non-infectious dermatosis, still more preferably, prevention, treatment or amelioration effect on psoriasis or atopic dermatitis.

What is claimed:

1. A method for preventing, treating and ameliorating dermatosis except for itching comprising administering a pharmacologically effective amount of a glycerol derivative represented by the formula (I) or a pharmacologically acceptable salt thereof to a person suffering from the dermatosis except for itching

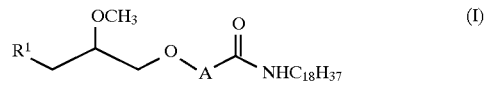

wherein A is a group represented by the formula:

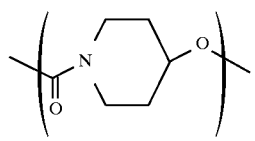

or single bond;

$R^1$ is a group represented by the formula:

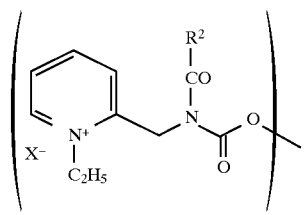

wherein $R^2$ is a methoxyphenyl group or methyl group, X is an atom or atomic group which may become an anion or group represented by the formula:

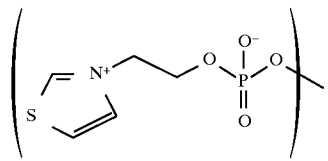

2. The method as claimed in claim 1, in which the dermatosis is non-infectious dermatosis.

3. The method as claimed in claim 1, in which the dermatosis is psoriasis or atopic dermatitis.

4. The method as claimed in claim 1, in which the glycerol derivative (I) is a pharmacologically acceptable salt of 1-ethyl-2-[N-(2-methoxy)benzoyl-N-{2-methoxy-3-(4-octadecylcarbamoyloxy) piperidinocarbonyloxypropoxy} carbonyl]aminomethyl pyridinium represented by the formula:

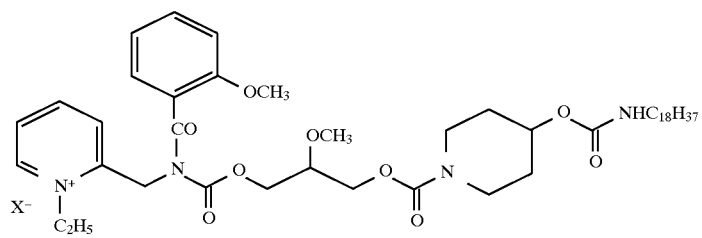
wherein X is as defined above.
5. The method as claimed in claim 1, in which the glycerol derivative (I) is 1-ethyl-2-[N-(2-methoxy)benzoyl-N-{(2R)-2-methoxy-3-(4-octadecylcarbamoyloxy) piperidinocarbonyloxypropoxy} carbonyl] aminomethylpyridinium chloride (II) represented by the formula:
(II)
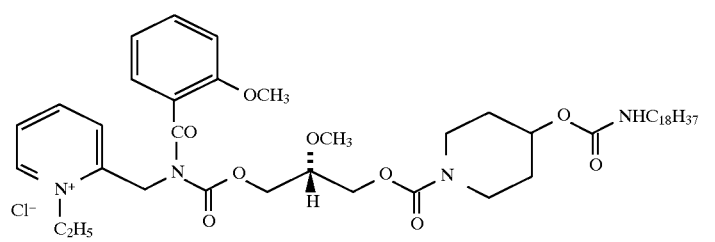
* * * * *